(12) United States Patent
Yang

(10) Patent No.: US 12,152,923 B2
(45) Date of Patent: Nov. 26, 2024

(54) URINE MONITORING METHOD AND PHYSIOLOGICAL MONITORING SYSTEM

(71) Applicants: Mikotek Information Inc., Taipei (TW); Ching-Wen Yang, Taipei (TW)

(72) Inventor: Ching-Wen Yang, Taipei (TW)

(73) Assignees: Mikotek Information Inc., Taipei (TW); Ching-Wen Yang, Taipei (TW)

( * ) Notice: Subject to any disclaimer, the term of this patent is extended or adjusted under 35 U.S.C. 154(b) by 376 days.

(21) Appl. No.: 17/457,430

(22) Filed: Dec. 2, 2021

(65) Prior Publication Data

US 2022/0412789 A1    Dec. 29, 2022

(30) Foreign Application Priority Data

Jun. 25, 2021   (TW) .................................. 110123305

(51) Int. Cl.
| | | |
|---|---|---|
| *G01F 23/20* | (2006.01) | |
| *A61M 5/168* | (2006.01) | |
| *G01F 23/80* | (2022.01) | |
| *G08B 21/18* | (2006.01) | |
| *H04L 67/10* | (2022.01) | |

(52) U.S. Cl.
CPC ......... *G01F 23/205* (2013.01); *A61M 5/1689* (2013.01); *G01F 23/804* (2022.01); *G08B 21/182* (2013.01); *A61M 2205/3553* (2013.01); *H04L 67/10* (2013.01)

(58) Field of Classification Search
CPC .............................. G01F 23/205; G01F 23/804
See application file for complete search history.

(56) References Cited

U.S. PATENT DOCUMENTS

| | | | |
|---|---|---|---|
| 2006/0235353 A1* | 10/2006 | Gelfand ................. | A61B 5/208 |
| | | | 604/67 |
| 2006/0270971 A1* | 11/2006 | Gelfand ............. | A61M 5/1723 |
| | | | 604/151 |
| 2018/0110455 A1* | 4/2018 | Chang ..................... | A61B 5/208 |
| 2019/0030243 A1* | 1/2019 | Yang ................ | A61M 5/16845 |
| 2019/0069830 A1* | 3/2019 | Holt ........................ | A61B 5/208 |
| 2019/0365994 A1* | 12/2019 | Yang ...................... | G01G 19/14 |
| 2021/0125718 A1 | 4/2021 | Suzuki | |

FOREIGN PATENT DOCUMENTS

| | | |
|---|---|---|
| CN | 112438730 A | 3/2021 |
| TW | 201127362 A | 8/2011 |
| TW | M617894 U | 10/2021 |

* cited by examiner

*Primary Examiner* — Ricky Go
(74) *Attorney, Agent, or Firm* — CKC & Partners Co., LLC

(57) ABSTRACT

The present disclosure relates to a urine monitoring method adapted to a urine monitoring device and a cloud server. The urine monitoring method includes the urine monitoring device detecting a real-time weight, the urine monitoring device sending the real-time weight to the cloud server through a communication interface, and the cloud server determining whether the real-time weight is less than a lower bound of a current weight or is greater than an upper bound of the current weight. If the real-time weight is either less than the lower bound of the current weight or greater than the upper bound of the current weight, the cloud server sends a signal to set the urine monitoring device as a urine volume warning status.

16 Claims, 4 Drawing Sheets

URINE MONITORING METHOD AND PHYSIOLOGICAL MONITORING SYSTEM

CROSS-REFERENCE TO RELATED APPLICATION

This application claims priority to Taiwan Application Serial Number 110123305, filed Jun. 25, 2021, which is herein incorporated by reference in its entirety.

BACKGROUND

Field of Invention

The present invention relates to a urine monitoring method. More particularly, the present invention relates to a urine monitoring method and a physiological monitoring system used between a urine monitoring device and a cloud server.

Description of Related Art

The urination of a patient is an important indicator of how the patient recovers, but urination has to be recorded by the patient's family, nurse, or caretaker. In addition, providing that the patient consumes enough water every day, the ureter has to be monitored in case there is any blockage. In the circumstance where the patient consumes 100 c.c. of water every hour and the blockage of the ureter has lasted for four hours, the nurse has to check the situation. Moreover, the nurse normally has to empty the urine bag and record the urination before handing over to the next shift. The nurse and the patient's family are burdened with these tasks.

SUMMARY

The present disclosure provides a urine monitoring method, used between a urine monitoring device and a cloud server. The urine monitoring method includes measuring a real-time weight and transmitting the real-time weight to the cloud server through a communication interface by the urine monitoring device; and determining whether the real-time weight is smaller than a current minimum weight or is greater than a current maximum weight by the cloud server; if the real-time weight is smaller than the current minimum weight or is greater than the current maximum weight, the cloud server transmits a signal to the urine monitoring device to set the urine monitoring device to a urine volume warning status.

The present disclosure also provides a physiological monitoring system. The physiological monitoring system includes a cloud server and a urine monitoring device. The urine monitoring device is communicatively connected to the cloud server. The urine monitoring device includes a communication interface, a weight measuring module, a processor, and a warning module. The communication interface is configured to communicatively connect to the cloud server. The weight measuring module is configured to measure a real-time weight. The processor is electrically connected to the weight measuring module. The weight measuring module receives the real-time weight. The communication interface transmits the real-time weight to the cloud server. The warning module is electrically connected to the processor and configured to transmit a warning signal. The cloud server is configured to determine whether the real-time weight is smaller than a current minimum weight or is greater than a current maximum weight. If the real-time weight is smaller than the current minimum weight or is greater than the current maximum weight, the cloud server transmits a signal to set the urine monitoring device to a urine volume warning status.

BRIEF DESCRIPTION OF THE DRAWINGS

The invention can be more fully understood by reading the following detailed description of the embodiment, with reference made to the accompanying drawings as follows.

DETAILED DESCRIPTION

Figure 1A:
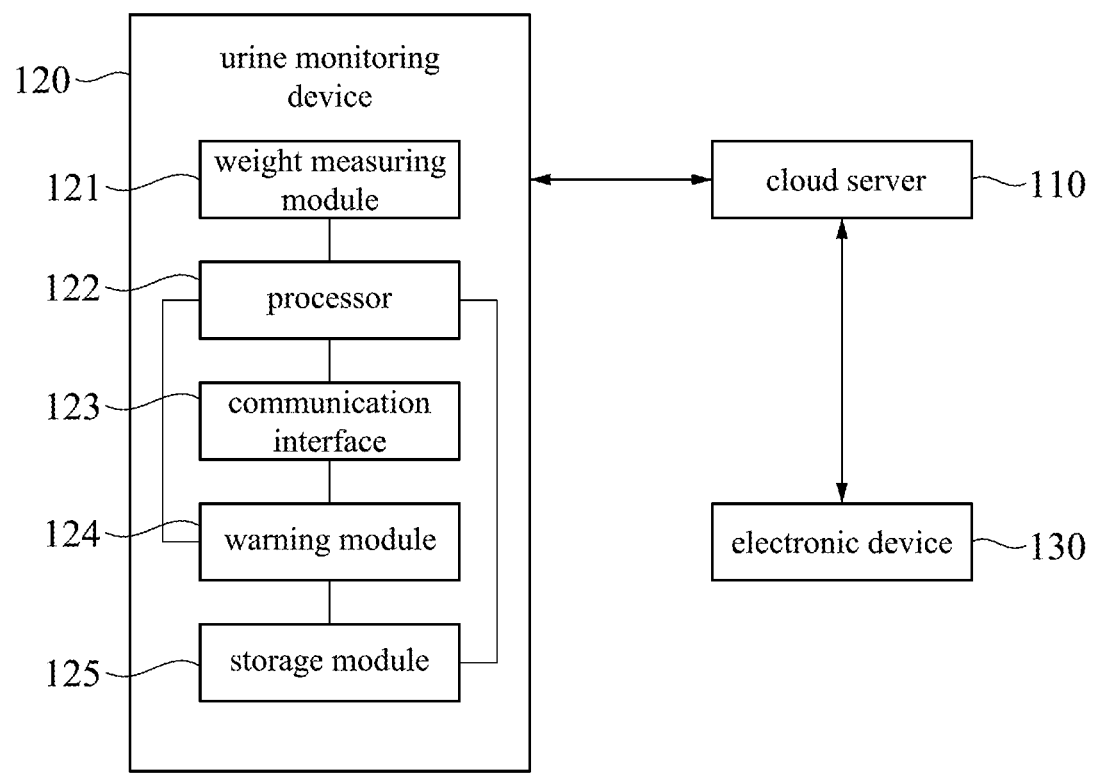
FIG. 1A is a schematic diagram of a physiological monitoring system in accordance with embodiments of the present disclosure.

Reference will now be made in detail to embodiments of the present disclosure, examples of which are described herein and illustrated in the accompanying drawings. While the disclosure will be described in conjunction with embodiments, it will be understood that they are not intended to limit the disclosure to these embodiments. On the contrary, the disclosure is intended to cover alternatives, modifications and equivalents, which may be included within the spirit and scope of the disclosure as defined by the appended claims. It is noted that, in accordance with the standard practice in the industry, the drawings are only used for understanding and are not drawn to scale. Hence, the drawings are not meant to limit the actual embodiments of the present disclosure. In fact, the dimensions of the various features may be arbitrarily increased or reduced for clarity of discussion. Wherever possible, the same reference numbers are used in the drawings and the description to refer to the same or like parts for better understanding.

In addition, in the following description and in the claims, the terms "include" and "comprise" are used in an open-ended fashion, and thus should be interpreted to mean "include, but not limited to." As used herein, the term "and/or" includes any and all combinations of one or more of the associated listed items.

In this document, the term "coupled" may also be termed "electrically coupled," and the term "connected" may be termed "electrically connected." "Coupled" and "connected" may also be used to indicate that two or more elements cooperate or interact with each other. It will be understood that, although the terms "first," "second," etc., may be used herein to describe various elements, these elements should not be limited by these terms. These terms are used to distinguish one element from another. They are not used to limit the order or limit the invention except that they are specifically indicated in the context.

The present disclosure provides a physiological monitoring system. Please refer to FIG. 1A. FIG. 1A is a schematic diagram of a physiological monitoring system 100 in accordance with embodiments of the present disclosure. The physiological monitoring system 100 includes a cloud server 110, a urine monitoring device 120, and an electronic device 130. The urine monitoring device 120 and the cloud server 110 are communicatively connected to each other. The urine monitoring device 120 includes a communication interface 123, a weight measuring module 121, a processor 122, a warning module 124, and a storage module 125. The communication interface 123 is configured to communicatively connect to the cloud server 110. The weight measuring module 121 measures a real-time weight of a urine bag. The processor 122 is electrically connected to the weight measuring module 121. The weight measuring module 121 receives the real-time weight and transmits the real-time weight to the cloud server 110 through the communication interface 123. The warning module 124 is electrically connected to the processor 122 and is configured to transmit warning signals. The storage module 125 is electrically connected to the processor 122 and is configured to store the real-time weight and other information. The cloud server 110 is configured to determine whether the real-time weight is smaller than a current minimum weight (the expected minimum weight of the urine bag at the current time) or larger than a current maximum weight (the expected maximum weight of the urine bag at the current time). If the real-time weight is smaller than the current minimum weight or larger than the current maximum weight, the cloud server 110 transmits a signal to the urine monitoring device 120 to set the urine monitoring device 120 to a urine volume warning status.

In one embodiment, a nurse or caretaker in a hospital can use the physiological monitoring system 100 to better monitor the status of the patient's urine bag, determine whether the patient's urination is abnormal or the urine bag is full, and take further action correspondingly. When mounted on the urine bag, the urine monitoring device 120 measures the real-time weight of the patient's urine bag through the weight measuring module 121, and the urine monitoring device 120 then transmits the real-time weight to the cloud server 110. Because the cloud server 110 can calculate an expected urination weight (the expected weight loss of the urine bag due to the patient's urination) according to the time that has passed since the urine bag was mounted, the cloud server 110 can determine whether the patient's urination is abnormal or the urine bag is full based on the real-time weight and the expected urination weight and send notification to the electronic device 130 held by the nurse or caretaker in cases where the patient's urination is abnormal or the urine bag is full. Accordingly, the physiological monitoring system 100 can monitor the patient's physiological status.

Figure 1B:
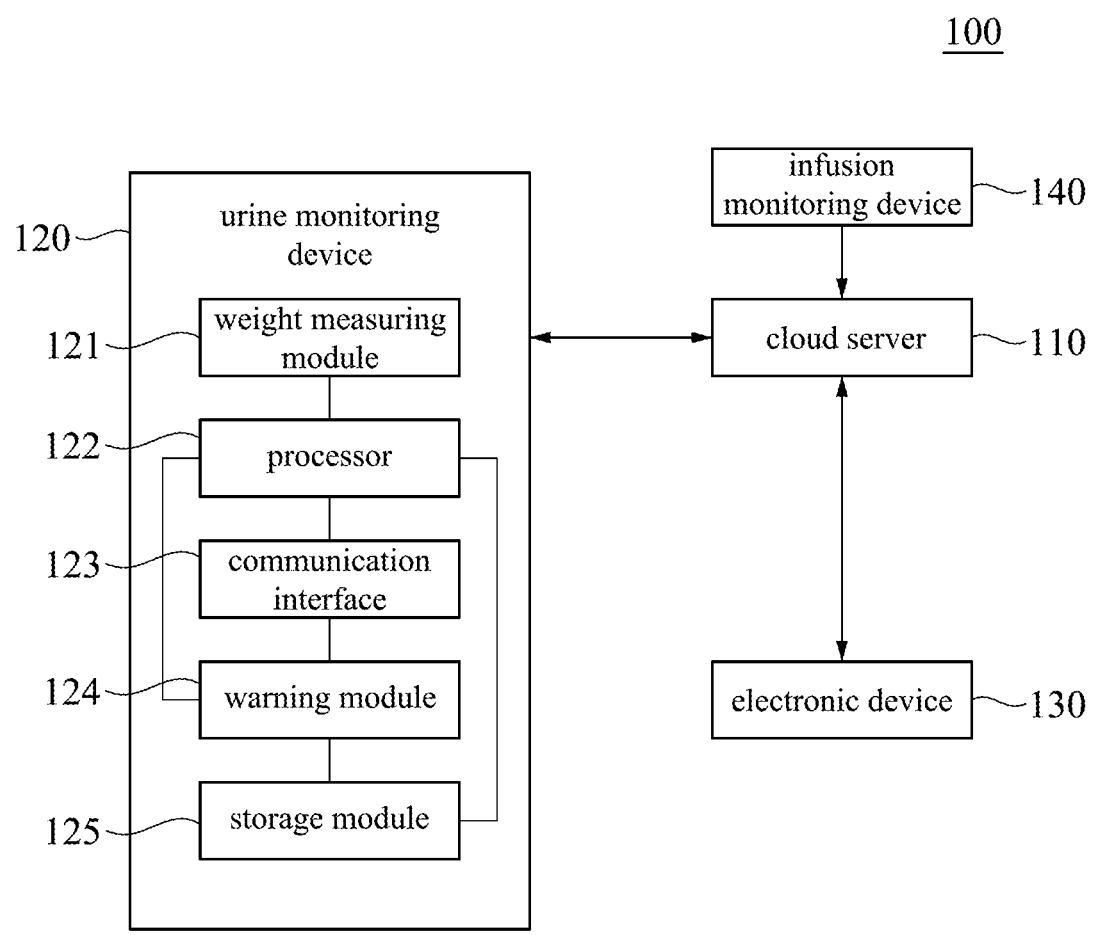
FIG. 1B is a schematic diagram of a physiological monitoring system in accordance with embodiments of the present disclosure.

Please refer to FIG. 1B. FIG. 1B is a schematic diagram of a physiological monitoring system 100 in accordance with embodiments of the present disclosure. In one embodiment, the physiological monitoring system 100 further includes an infusion monitoring device 140. The infusion monitoring device 140 is communicatively connected to the cloud server 110. The infusion monitoring device 140 is configured to monitor infusion monitoring information and transmit the infusion monitoring information to the cloud server 110. Then, the cloud server 110 calculates the current minimum weight according to the expected minimum urination weight (the expected minimum weight loss of the urine bag due to the patient's urination), an empty-bag weight (the weight of the urine bag when the urine bag is empty), a poured-out difference (the urine bag's weight difference due to the urine in the urine bag being poured out), and the infusion monitoring information, and calculates the current maximum weight according to the expected maximum urination weight (the expected maximum weight loss of the urine bag due to the patient's urination), the empty-bag weight, the poured-out difference, and the infusion monitoring information. In one embodiment, the infusion monitoring information detected by the infusion monitoring device 140 include the status of the intravenous drip, including information such as type of the administered medication and the speed of intravenous drip. If the administered medication has diuretic effect, the patient's urination will be affected. In this embodiment, the infusion monitoring device 140 will record this situation and send notification to the cloud server 110, so that the cloud server 110 can automatically calculate the patient's expected urination at a specific time according to the administered medication.

Below the above-mentioned steps and method implemented by the physiological monitoring system 100 to determine whether the patient's urination is abnormal or whether the urine bag is full will be illustrated in detail using embodiments.

Figure 2A:
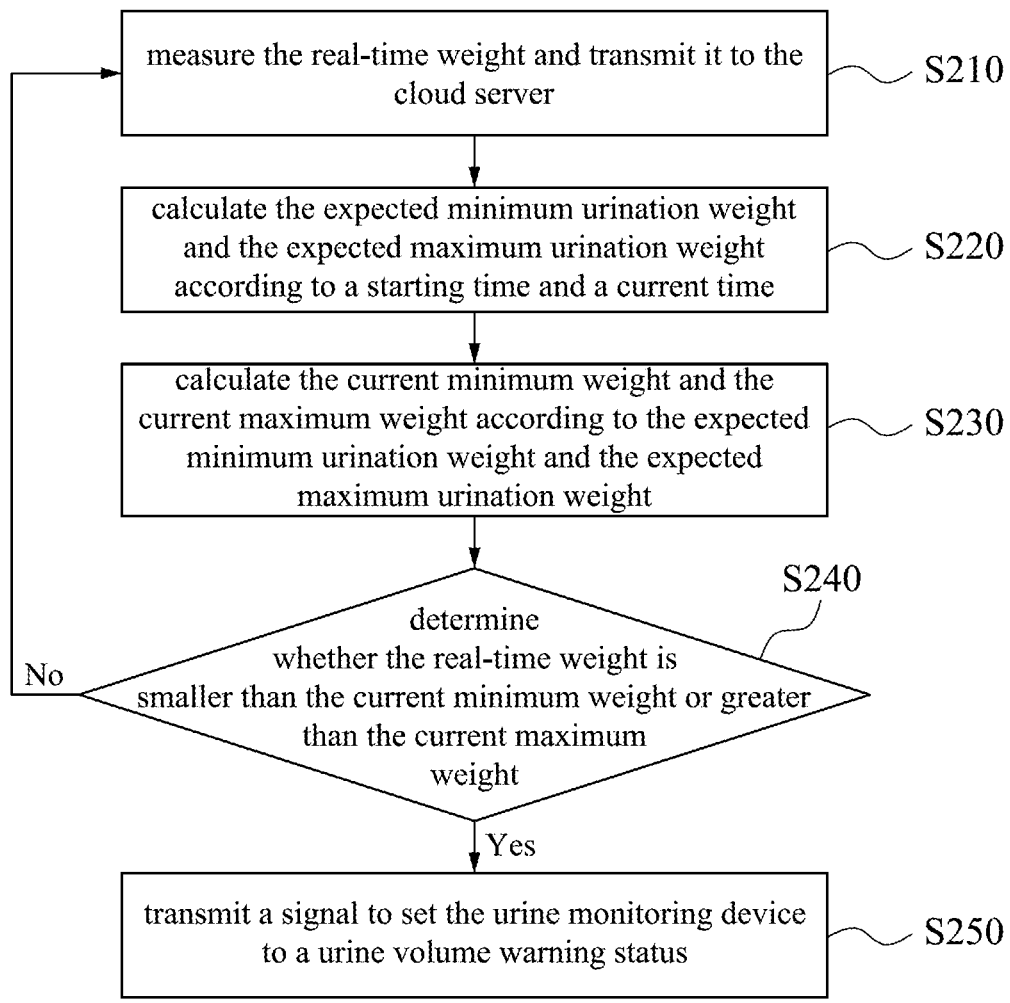
FIG. 2A is a flow chart of a urine monitoring method in accordance with embodiments of the present disclosure.

The present disclosure also provides a urine monitoring method. Please refer to FIG. 1A and FIG. 2A. FIG. 2A is a flow chart of a urine monitoring method 200 in accordance with embodiments of the present disclosure. The urine monitoring method 200 is used between the urine monitoring device 120 and the cloud server 110. In step S210, the urine monitoring device 120 measures the real-time weight through the weight measuring module 121 and transmits the real-time weight to the cloud server 110 through the communication interface 123. In step S220, the cloud server 110 calculates the expected minimum urination weight and the expected maximum urination weight according to a starting time and a current time. In step S230, the cloud server 110 calculates the current minimum weight according to the expected minimum urination weight and the empty-bag weight and calculates the current maximum weight according to the expected maximum urination weight and the empty-bag weight. In one embodiment, the empty-bag weight is the weight of a urine bag usually sold on the market, e.g. around 20 grams. In other words, the empty-bag weight is predetermined. In one embodiment, the empty-bag weights stored in the storage module 125. In step S240, the cloud server 110 determines whether the real-time weight is smaller than the current minimum weight or greater than the current maximum weight. Then, if the real-time weight is smaller than the current minimum weight or greater than the current maximum weight, in step S250, the cloud server 110 transmits a signal to the urine monitoring device through the communication interface 123 in order to set the urine monitoring device 120 to a urine volume warning status through the warning module 124, and continually monitors the real-time weight and transmits it to the cloud server 110.

In other words, the urine monitoring method 200 can be used accompanied with a system like the physiological monitoring system 100 to calculate the expected weight of the urine bag (i.e., the weight range from the current minimum weight to the current maximum weight) based the time passed and the empty-bag weight, continually monitor the actual weight of the urine bag (i.e., the real-time weight), compare the real-time weight with the expected weight, set the urine bag to the warning status when the weight of the urine bag is unreasonable (i.e., when the real-time weight is smaller than the current minimum weight or when the real-time weight is greater than the current maximum weight), and keep monitoring the weight of the urine bag if there is no any abnormality in terms of the weight of the urine bag.

In one embodiment, the urine monitoring method 200 can detect whether the urine has been poured away from the urine bag and modify the current minimum weight and the current maximum weight according to the volume of the urine that has been poured away (i.e., the poured-out difference mentioned below). In this embodiment, the urine monitoring method 200 further includes using the cloud server 110 to determine whether the real-time weight is smaller than a last-time weight (the real-time weight that the urine monitoring device 120 measured through the weight measuring module 121 last time) and, when the real-time weight is smaller than the last-time weight (i.e., when the urine has been poured away from the urine bag), to calculate a poured-out difference according to the real-time weight and the last-time weight. Then, the cloud server 110 calculates the current minimum weight according to the expected minimum urination weight, the empty-bag weight, and the poured-out difference and calculates the current maximum weight according to the expected maximum urination weight, the empty-bag weight, and the poured-out difference. Therefore, the current minimum weight and the current maximum weight are corrected. Moreover, in this embodiment, the urine monitoring method 200 can further include calculating the total amount of the urine that has been poured away from the urine bag. In this embodiment, the urine monitoring method 200 can further include using the cloud server 110 to accumulate the poured-out difference to calculate the total urination weight.

Please refer to FIG. 1B and FIG. 2A. In one embodiment, the urine monitoring method 200 further includes modifying the current minimum weight and the current maximum weight in cases where the patient has been given infusion. In one embodiment, the urine monitoring method 200 further includes using the infusion monitoring device 140 to monitor infusion monitoring data and transmit the infusion monitoring data to the cloud server 110. The cloud server 110 then calculates the current minimum weight according to the expected minimum urination weight, the empty-bag weight, the poured-out difference, and the infusion monitoring data and calculates the current maximum weight according to the expected maximum urination weight, the empty-bag weight, the poured-out difference, and the infusion monitoring data. By doing so, the infusion that the patient has been given are considered, and the current minimum weight and the current maximum weight are corrected. In one embodiment, the infusion monitoring data that the infusion monitoring device 140 monitors include the status of the intravenous drip, e.g., information such as the administered medication and speed of intravenous drip, and the infusion monitoring device 140 transmits such information to the cloud server 110. The cloud server 110 then automatically calculates a patient's expected urination at a specific time according to the administered medication.

Figure 2B:
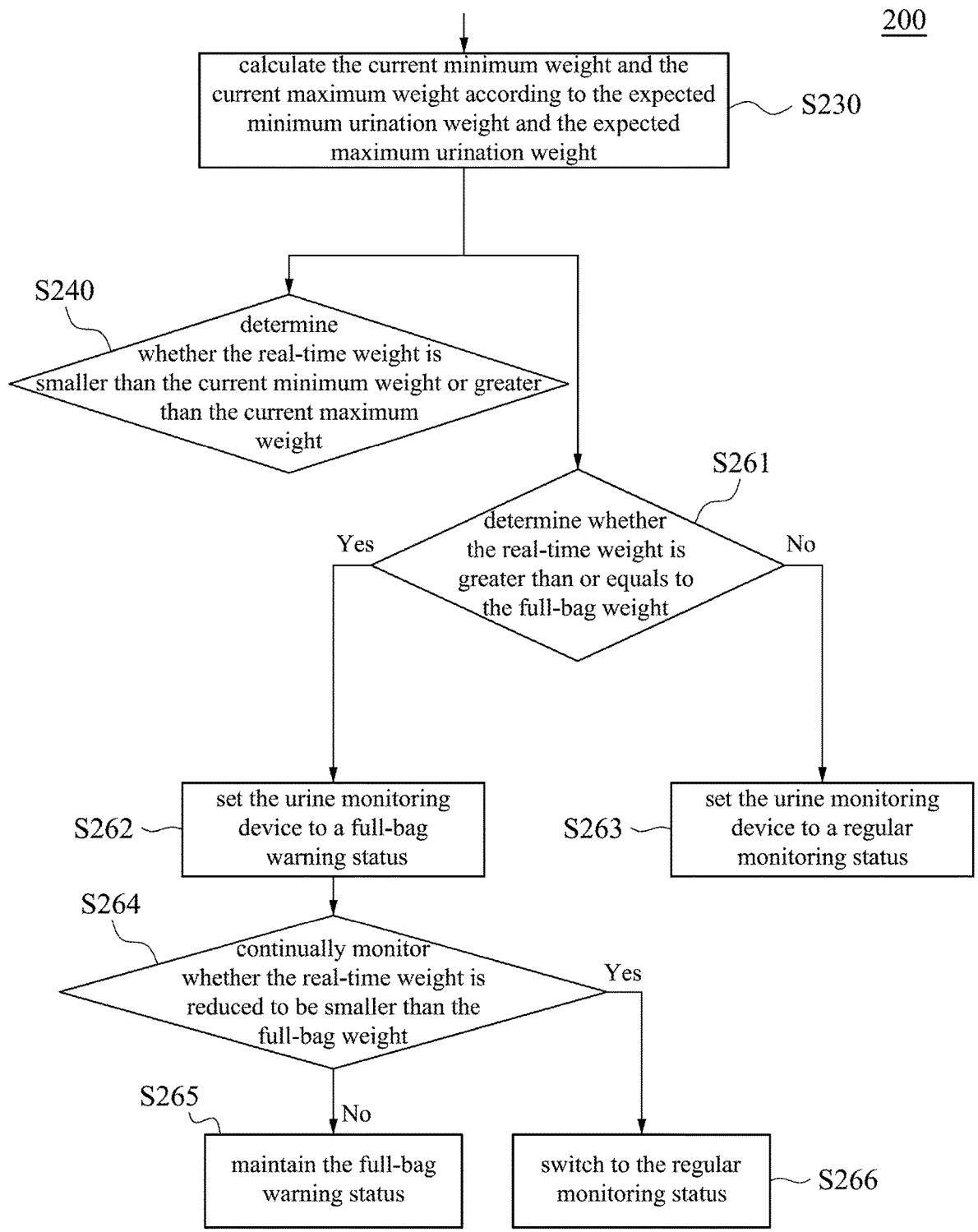
FIG. 2B is a flow chart of a urine monitoring method in accordance with embodiments of the present disclosure.

Please refer to FIG. 1A, FIG. 2A, and FIG. 2B. FIG. 2B is a flow chart of a urine monitoring method 200 in accordance with embodiments of the present disclosure. In one embodiment, the monitoring method 200 can not only monitor whether there is discrepancy between the actual urination and the expected urination but also detect whether the urine bag is full. If the urine bag is full, the urine monitoring method 200 will send out a warning, monitor whether the urine has been poured away from the bag and the warning can be cancelled, record the volume of the poured-away urine, and transmit it to the cloud server 110 in order to calculate the current minimum weight and current maximum weight. In this embodiment, the urine monitoring method 200 further includes steps S261, S262, S263, and S264. As shown in FIG. 2A, after calculating the current maximum weight and current minimum weight in step S230, the urine monitoring method 200 in step S240 determines whether the real-time weight is smaller than the current minimum weight or is greater than the current maximum weight. In one embodiment, as shown in FIG. 2B, after step S230 is performed, the urine monitoring method 200 can perform either step S240 and subsequent steps (such as step S250 shown in FIG. 2A) or perform steps S261, S262, S263, S264, S265, and S266. Step S240 does not have to be performed before steps S261, S262, S263, S264, S265, and S266, and vice versa. Moreover, in some embodiments, steps S261, S262, S263, S264, S265, and S266 can be performed before step S230. For example, the determination about whether the urine bag is full that is implemented by steps S261, S262, S263, S264, S265, and S266 can be performed right after the real-time weight is measured in step S210. Person having ordinary skills in the related art can adjust or modify the order of the steps included in the urine monitoring method 200 according to real needs, and such adjustment or modification should be recognized as having been disclosed in the present disclosure.

In step S261, the urine monitoring method 200 determines whether the real-time weight is greater than or equals to the full-bag weight. In one embodiment, the full-bag weight can be set up according to the capacity of different urine bags that are on the market. For example, for a urine bag of which the capacity is 500 ml, the full-bag weight can be set as 450 ml. In step S262, when the real-time weight is greater than or equals to the full-bag weight, the urine monitoring device 120 is set to a full-bag warning status. In step S263, when the real-time weight is smaller than the full-bag weight, the urine monitoring device 120 is set to be a regular monitoring status.

In this embodiment, when the urine monitoring device 120 is in the full-bag warning status, the urine monitoring method 200 can further include steps S264, S265, and S266. In step S264, the urine monitoring device 120 continually monitors whether the real-time weight is reduced to be smaller than the full-bag weight. In step S265, if the real-time weight is not reduced to be smaller than the full-bag weight, the full-bag warning status of the urine monitoring device 120 is maintained. In step 266, if the real-time weight is reduced to be smaller than the full-bag weight, the urine monitoring device 120 cancels the full-bag warning status and switches to the regular monitoring status. It should be noted that, as previously described, the urine monitoring method 200 can detect whether the urine has been poured away from the urine bag, calculate the poured-out difference according to the real-time weight and the last-time weight, and modify the current minimum weight and the current maximum weight according to the volume of the urine that has been poured away by the cloud server 110. Therefore, if the urine has been poured away from the urine bag in step S264, S265, and/or S266, the urine monitoring device 120 will transmit the real-time weights before and after the urine has been poured away to the cloud server 110 through the communication interface 123, and the cloud server 110 will calculate the poured-out difference by subtracting the real-time weight after the urine has been poured away from the real-time weight before the urine has been poured away and calculate the current minimum weight and the current maximum weight according to the poured-out difference. In one embodiment, the step S230 in FIG. 2A considers, in addition to the expected maximum urination weight, the expected minimum urination weight, and the empty-bag weight, the poured-out difference while calculating the current minimum weight and the current maximum weight.

In one embodiment, the urine monitoring method 200 can adjust the full-bag weight according to the urine bags with different capacity. In this embodiment, the urine monitoring method 200 further includes receiving a mode setting signal and setting the full-bag weight as one of a plurality of full-bag weights according to the mode setting signal by the processor 122. In practice, the urine monitoring device 120 can include an input interface for user to set the adequate full-bag weight by giving a command to the electronic device 130 through the input interface according to the urine bag that is used by the user, or alternatively, the full-bag weight can be set up through the electronic device 130 communicatively connecting to the cloud server 110 and the cloud server 110 communicatively connecting to the urine monitoring device 120.

Although the present invention has been described in considerable detail with reference to certain embodiments thereof, other embodiments are possible. Therefore, the spirit and scope of the appended claims should not be limited to the description of the embodiments contained herein. It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. A urine monitoring method, used between a urine monitoring device and a cloud server, comprising:
   measuring a real-time weight and transmitting the real-time weight to the cloud server through a communication interface by the urine monitoring device;
   determining whether the real-time weight is smaller than a current minimum weight or is greater than a current maximum weight by the cloud server, further comprising:
      calculating an expected minimum urination weight and an expected maximum urination weight by the cloud server according to a starting time and a current time; and
      determining whether the real-time weight is smaller than a last-time weight and, in response to the real-time weight being smaller than the last-time weight, calculating a poured-out difference according to the real-time weight and the last-time weight by the cloud server;
      calculating the current minimum weight by the cloud server according to the expected minimum urination weight, the empty-bag weight, and the poured-out difference; and
      calculating the current maximum weight by the cloud server according to the expected maximum urination weight, an empty-bag weight, and the poured-out difference; and
   generating a signal by the cloud server when the real-time weight is smaller than the current minimum weight or is greater than the current maximum weight, the cloud server transmits the signal to the urine monitoring device, so as to set the urine monitoring device to a urine volume warning status to send a notification to a user to check whether there is discrepancy between an actual urination and an expected urination.

2. The urine monitoring method of claim 1, further comprising:
   determining whether the real-time weight is greater than or equals to a full-bag weight by the urine monitoring device and, in response to the real-time weight being greater than or equaling to a full-bag weight, setting the urine monitoring device to a full-bag warning status.

3. The urine monitoring method of claim 2, further comprising:
   setting the urine monitoring device to a regular monitoring status in response to the real-time weight being smaller than the full-bag weight.

4. The urine monitoring method of claim 2, wherein, in response to the urine monitoring device being set to the full-bag warning status, the urine monitoring method further comprising:
   continually monitoring whether the real-time weight is reduced to be smaller than the full-bag weight by the urine monitoring device;
   maintaining the full-bag warning status in response to the real-time weight not being reduced to be smaller than the full-bag weight; and
   switching the urine monitoring device to a regular monitoring status in response to the real-time weight being reduced to be smaller than the full-bag weight.

5. The urine monitoring method of claim 2, further comprising:
   receiving a mode setting signal and setting the full-bag weight as one of a plurality of full-bag weights according to the mode setting signal by a processor.

6. The urine monitoring method of claim 1, wherein an infusion monitoring device detects infusion monitoring data and transmits the infusion monitoring data to the cloud server, and the cloud server calculates the current minimum weight according to the expected minimum urination weight, the empty-bag weight, the poured-out difference, and the infusion monitoring data and calculates the current maximum weight according to the expected maximum urination weight, the empty-bag weight, the poured-out difference, and the infusion monitoring data.

7. The urine monitoring method of claim 6, wherein the infusion monitoring data comprise information about administered medication and speed of intravenous drip, and the cloud server automatically calculates a patient's expected urination at a specific time according to the administered medication.

8. The urine monitoring method of claim 1, wherein the cloud server accumulates the poured-out difference to calculate a total urination weight.

9. A physiological monitoring system, comprising:
   a cloud server; and
   a urine monitoring device, communicatively connected to the cloud server, comprising:
      a communication interface, configured to communicatively connect to the cloud server;
      a weight measuring module, configured to measure a real-time weight;
      a processor, electrically connected to the weight measuring module, the weight measuring module receiving the real-time weight, the communication interface transmitting the real-time weight to the cloud server; and
      a warning module, electrically connected to the processor and configured to transmit a warning signal;
   wherein the cloud server is configured to determine whether the real-time weight is smaller than a current minimum weight or is greater than a current maximum weight, further comprises:
      the cloud server calculates an expected minimum urination weight and an expected maximum urination weight according to a starting time and a current time;
      the cloud server determines whether the real-time weight is smaller than a last-time weight and, in response to the real-time weight being smaller than the last-time weight, calculates a poured-out difference according to the real-time weight and the last-time weight; and the cloud server calculates the current minimum weight according to the expected minimum urination weight, an empty-bag weight, and the poured-out difference and calculates the current maximum weight according to the expected maximum urination weight, the empty-bag weight, and the poured-out difference; and the cloud server generates a signal when the real-time weight is smaller than the current minimum weight or is greater than the current maximum weight, and the cloud server transmits the signal to the urine monitoring device, so as to set the urine monitoring device to a urine volume warning status to send a notification to a user to check whether there is discrepancy between an actual urination and an expected urination.

10. The physiological monitoring system of claim 9, wherein the processor determines whether the real-time weight is greater than or equals to a full-bag weight and, in response to the real-time weight being greater than or equaling to the full-bag weight, sets the urine monitoring device to a full-bag warning status.

11. The physiological monitoring system of claim 10, wherein the processor sets the urine monitoring device to a regular monitoring status in response to the real-time weight being smaller than the full-bag weight.

12. The physiological monitoring system of claim 10, wherein, in response to the urine monitoring device being set to the full-bag warning status, the processor continually monitors whether the real-time weight is reduced to be smaller than the full-bag weight;

the processor maintains the full-bag warning status of the urine monitoring device in response to the real-time weight not being reduced to be smaller than the full-bag weight;

the processor switches the urine monitoring device to a regular monitoring status in response to the real-time weight being reduced to be smaller than the full-bag weight.

13. The physiological monitoring system of claim 10, wherein the processor receives a mode setting signal and sets the full-bag weight as one of a plurality of full-bag weights according to the mode setting signal.

14. The physiological monitoring system of claim 9, further comprising:

an infusion monitoring device, communicatively connected to the cloud server and configured to monitor infusion monitoring data and transmit the infusion monitoring data to the cloud server, the cloud server calculating the current minimum weight according to the expected minimum urination weight, the empty-bag weight, the poured-out difference, and the infusion monitoring data and calculating the current maximum weight according to the expected maximum urination weight, the empty-bag weight, the poured-out difference, and the infusion monitoring data.

15. The physiological monitoring system of claim 14, wherein the infusion monitoring data comprise information about the administered medication and speed of intravenous drip, and the cloud server automatically calculates a patient's expected urination at a specific time according to the administered medication.

16. The physiological monitoring system of claim 9, wherein the cloud server accumulates the poured-out difference to calculate a total urination weight.

* * * * *